US006987013B2

(12) United States Patent
Hummel et al.

(10) Patent No.: US 6,987,013 B2
(45) Date of Patent: Jan. 17, 2006

(54) NADH OXIDASE FROM LACTOBACILLUS

(75) Inventors: Werner Hummel, Titz (DE); Bettina Bommarius, Atlanta, GA (US)

(73) Assignee: Degussa AG, Duesseldorf (DE)

( * ) Notice: Subject to any disclaimer, the term of this patent is extended or adjusted under 35 U.S.C. 154(b) by 385 days.

(21) Appl. No.: 10/219,288

(22) Filed: Aug. 16, 2002

(65) Prior Publication Data

US 2003/0100065 A1 May 29, 2003

(30) Foreign Application Priority Data

Aug. 16, 2001 (DE) ......................................... 101 40 088

(51) Int. Cl.
*C12N 9/04* (2006.01)
*C07H 21/04* (2006.01)

(52) U.S. Cl. ..................................... 435/190; 536/23.2
(58) Field of Classification Search ................. 435/190, 435/440, 6, 69.1; 536/23.2
See application file for complete search history.

(56) References Cited

FOREIGN PATENT DOCUMENTS

WO    WO 01/23582 A1    4/2001

OTHER PUBLICATIONS

Conn et al. Biochemistry, vol. 37, pp. 8790–8802, 1998.*
Database EMBL. Dec. 15., 2000. Knorr et al., "Genomic Region of the Gene Encoding for a Putative NADH Oxidase from *Lactobacillus sanfranciscensis*", Database Accession No. AB035801, XP002219891.
Database EMBL. Feb. 3, 1993. Ross and Claiborne, "Molecular Cloning and Analysis of the Gene Encoding the NADH Oxidase from *Streptococcus Faecalis* 10C1". Database Accession No. X68847, XP002219892.
Xianwen Yi, et al., "Properties of NADH Oxidase for *Lactobacillus delbrueckir* ssp bulgaricus", *J. Sci. Food Argric.*, 1998. vol. 78. 527–534, XP-002219890.

* cited by examiner

*Primary Examiner*—Ponnathapu Achutamurthy
*Assistant Examiner*—Yong D. Pak
(74) *Attorney, Agent, or Firm*—Oblon, Spivak, McClelland, Maier & Neustadt, P.C.

(57) ABSTRACT

The present invention is directed to a new NADH oxidase from Lactobacillus, nucleic acids encoding the NADH oxidase, methods of producing the NADH oxidase, as well as there use in producing improved NADH oxidase enzymes and for producing chrial enantiomer-enriched organic compounds, such as alcohols and/or amino acids.

3 Claims, 2 Drawing Sheets

NADH OXIDASE FROM LACTOBACILLUS

FIELD OF THE INVENTION

The present invention relates to an NADH oxidase from Lactobacillus, as well as the nucleic acids coding for this enzyme and vehicles containing these nucleic acids. In particular the invention relates to an oxidase from *Lactobacillus brevis* (DSM 20054).

BACKGROUND OF THE INVENTION

Dehydrogenases, classified under E.C. 1.1, are enzymes that reversibly catalyse the oxidation or reduction of certain compounds such as for example alcohols and ketones. Some of the known dehydrogenases are cofactor-dependent, in other words they require further molecules to balance the electron transfer processes. NADH and NADPH for example are known to be such cofactors.

NADH is formed in the oxidation of, for example, alcohols to ketones according to the following reaction scheme. In order to avoid having to add stoichiometric amounts of expensive NAD+, the formation of NAD+ can be initiated by a second enzyme system (Enzyme Catalysis in Organic Synthesis, Ed.: K. Drauz, H. Waldmann, VCH, 1$^{st}$ Edition, p. 721; reaction scheme 1).

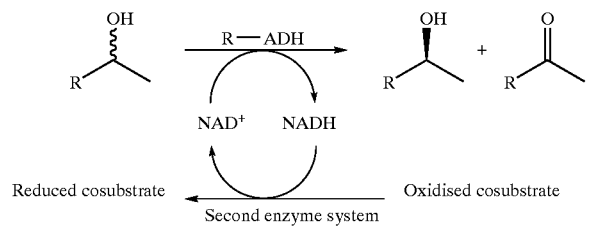

Systems known previously described using lactate dehydrogenase and pyruvate with the formation of lactate, or glutamate dehydrogenase with ketoglutarate and ammonium with the formation of glutamate for regenerating NAD+. The disadvantage of these systems is that auxiliary substrates, such as pyruvate or ketoglutarate, have to be used and products, such as lactate or glutamate, are formed, which for preparative utilization have to be removed from the product. In addition, equilibrium reactions go to completion only with great technical difficulty.

Alternatively, a second enzyme system may be an NADH oxidase that accepts atmospheric oxygen as oxidised cosubstrate and at the same time generates water or hydrogen peroxide with the formation of NAD+. In this respect, NADH oxidases are advantageous in that the reaction catalyzed by them is irreversible, $O_2$ is used as regeneration substrate, and $H_2O$ or $H_2O_2$ are formed as product. Enzymes of both groups ($H_2O$-forming and $H_2O_2$-forming enzymes) are, in principle, known in the biochemical literature (for example, for $H_2O$-forming enzymes see Lopez de Felipe, F. et al., *J. Bacteriol.* Vol. 180 (1998), 3804–08; for $H_2O_2$-forming enzymes see Nishiyama, Y. et al. *J. Bacteriol.* Vol. 183 (2001), 2431–2438 and the literature cited therein). $H_2O_2$-forming enzymes are less suitable as a regeneration enzyme since peroxide is known to be harmful to enzymes and should be decomposed as far as possible in situ, which requires further, disadvantageous but not impossible process steps.

The NADH oxidases from *Enterococcus* (and *Streptococcus*) *faecalis* (Schmidt, H. L. et al., *Eur. J. Biochem.* 156 (1986), 149–55), *Leuconostoc mesenteroides* (Koike K. J. et al., *Biochem.* (Tokyo) 97 (1985), 1279–88), *Streptococcus mutans* (Higuchi, M. et al., *Biosci. Biotechnol. Biochem.* 58 (1994), 1603–07), *Mycoplasma capricolum* (Klomkes M., Altdorf, R., Ohlenbusch, H. D., *Biol. Chem. Hoppe Seyler* 366 (1985), 963–9), *Sulfolobus solfataricus* (Arcari P. et al., *J. Biol. Chem.* 275 (2000), 895–900), *Thermus thermophilus* (Erdmann, H. et al., *J. Mol. Biol.* 230 (1993), 1086–8) and from *Thermus aquaticus* (Cocco, D. et al., *Eur. J. Biochem.* 174 (1988), 267–71) have been biochemically characterised.

However, there remains a need in the art for NADH oxidase with high activity, stability, etc. that when coupled with a dehydrogenase can be used for NAD+ regeneration.

SUMMARY OF THE INVENTION

Therefore, an object of the present invention is to provide an NADH oxidase with high activity that is suitable when coupled with dehydrogenases for NAD+ regeneration. In particular the NADH oxidase should be able to be produced easily and should be available in sufficient amount for advantageous use on an industrial scale.

Another object of the invention is an isolated NADH oxidase obtained from Lactobacillus, preferably from *Lactobacillus brevis*, more preferably *Lactobacillus brevis* DSM 20054. In one embodiment of the present invention, the NADH oxidase has the amino acid sequence in SEQ ID NO:2.

Another object of the invention are those nucleic acid sequences that encode the NADH oxidase, as well as vectors and host cells containing the same. In one embodiment the nucleic acid sequence is SEQ ID NO:1.

Another object of the invention is for a process for producing a rec-NADH oxidase, by cultivating a host cell containing the nucleic acid, which encodes the rec-NADH oxidase and collecting the rec-NADH oxidase produced.

Another object of the present invention is a process for producing a rec-NADH oxidase by mutating a nucleic acid encoding the rec-NADH oxidase; screening the mutated nucleic acid obtained in an expression system, which allows protein encoded by the nucleic acid sequence to be expressed; detecting a mutated nucleic acid that encodes an rec-NADH oxidase with improved activity; and isolating the mutated nucleic acid that encodes an rec-NADH oxidase with improved activity. Therefore, another object of the present invention are those rec-NADH oxidases obtained by these processes, as well as, vectors, host cells, and uses therein.

Another object of the present invention is for a method of producing a chiral enantiomer-enriched organic compound by contacting/reacting the organic compound with the rec-NADH oxidase described herein.

Another object of the invention is a whole-cell catalyst containing the rec-NADH oxidase and/or a nucleic acid encoding the oxidase; which catalyst may also contain a dehydrogenase and/or a nucleic acid encoding the dehydrogenase.

DETAILED DESCRIPTION OF THE INVENTION

Figure 1:
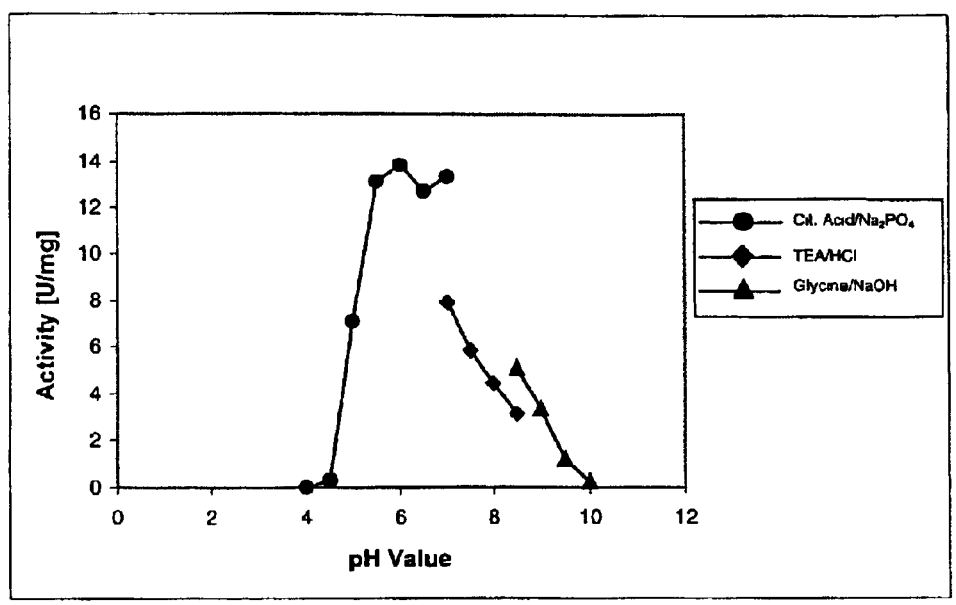
FIG. 1 shows the optimum pH of NADH oxidation.

Unless otherwise defined, all technical and scientific terms used herein have the same meaning as commonly understood by one of ordinary skill in the art of molecular biology. Although methods and materials similar or equivalent to those described herein can be used in the practice or testing of the present invention, suitable methods and materials are described herein. All publications, patent applications, patents, and other references mentioned herein are incorporated by reference in their entirety. In addition, the materials, methods, and examples are illustrative only and are not intended to be limiting.

Since an NADH oxidase (NOX) from Lactobacillus species is now available, it is possible advantageously to achieve the aforementioned object. Most particularly preferred is the use of an NADH oxidase (NOX) from *Lactobacillus brevis*, preferably DSM 20054 (SEQ ID NO:2), which is encoded by the nucleic acid of SEQ ID NO:1 or *Lactobacillus kefir* (EP 91107067.0; DE 4014573).

The NADH oxidase is able to convert the NADH formed in the reaction into NAD+, according to the reaction scheme shown in the Background of the Invention section of this application. On account of the irreversibility of the reaction $O_2$ to $H_2O$, there is a complete conversion of the employed racemic alcohol to ketone due to the equilibrium pressure, a highly enantiomer-enriched unreacted optical antipode of the employed alcohol remaining. Examples of the use of the NADH oxidase (NOX) include, inter alia, the production of R-alcohols when coupled with an S-alcohol dehydrogenase, of S-alcohols when coupled with an R-alcohol dehydrogenase, or the production of D-amino acids when coupled with an L-amino acid dehydrogenase. The coupling with hydroxyacid dehydrogenases and all other NAD-dependent dehydrogenases is also possible in this context. As further important products there may also be mentioned the oxidation products of the dehydrogenase reaction, for example ketones, keto acids or aldehydes.

In another embodiment, the invention is concerned with nucleic acids coding for an NADH oxidase according to the invention.

In spite of the relative ease of cultivation of the Lactobacillus strains and easy accessibility of the enzyme via chromatographic methods, it has become possible by specifying the nucleic acids coding for an NADH oxidase (NOX) according to the invention to obtain, in a furthermore preferred way and manner, substances that enable the enzymes necessary for an enzymatic industrial process for the production of enantiomer-enriched compounds to be made available in sufficient amounts via recombinant techniques. It is possible with the nucleic acids to obtain the enzymes in high yields from rapidly growing host organisms. Also, the gene sequences according to the invention have to be employed for the production of improved mutants.

In another embodiment, the invention relates to plasmids or vectors containing one or more of the nucleic acids according to the invention.

As plasmids or vectors there may, in principle, be used all embodiments for this purpose available to the person skilled in the art. Such plasmids and vectors may be found in the article by Studier et al., *Methods Enzymol.* 1990, 185, 61–69 or in the brochures published by the companies Novagen, Promega, New England Biolabs, Clontech or Gibco BRL. Further preferred plasmids and vectors may be found in: DNA cloning: A Practical Approach. Volume I–III, edited by D. M. Glover, IRL Press Ltd., Oxford, Washington D.C., 1985, 1987; Denhardt, D. T. and Colasanti, J.: A survey of vectors for regulating expression of cloned DNA in E. coli. In: Rodriguez, R. L. and Denhardt, D. T (eds), Vectors, Butterworth, Stoneham, Mass., 1987, pp179–204; Gene expression technology. In: Goeddel, D. V. (eds), Methods in Enzymology, Volume 185, Academic Press, Inc., San Diego, 1990; Sambrook, J., Fritsch, E. F. and Maniatis, T. 1989. Molecular cloning: A Laboratory Manual, $2^{nd}$ ed., Cold Spring Harbor Laboratory Press, Cold Spring Harbor, N.Y.

Preferable plasmids include: pKK-177-3H (Roche Biochemicals), pBTac (Roche Biochemicals), pKK-233 (Stratagene) or pET (Novagen). With the exception of the TOPO series, which has integrated a resistance to kanamycin, all other plasmids should contain a β-lactamase for ampicillin resistance.

The invention also provides microorganisms containing the nucleic acids according to the invention.

The microorganism in which the nucleic acids are cloned serves for the propagation and production of a sufficient amount of the recombinant enzyme. The processes for this are well known to the person skilled in the art (see below). Examples of such microorganisms include, for example, prokaryotes or eukaryotes, such as Pseudomonas, Streptomyces, Arthrobacter, Bacillus, Staphylococcus, *E. coli*, Candida, Hansenula, Pichia and baculoviruses. *E. coli* strains are preferably used. Most particularly preferred are: *E. coli* NM 522, JM109, JM105, RR1, DH5α, TOP 10- or HB101. Plasmids with which the gene construct containing the nucleic acid according to the invention is preferably cloned in the host organism are disclosed above.

The invention also includes nucleic acids that hybridize under stringent conditions with the single-strand nucleic acids according to the invention or with their complementary single-strand nucleic acids. The expression "stringent conditions" is understood to be the conditions described by Sambrook et al. (Molecular Cloning, A Laboratory Manual, Cold Spring Harbor Laboratory Press (1989), 1.101–1.104). Preferably a stringent hybridisation takes place according to the present invention if, after washing for one hour with 1×SSC and 0.1% SDS (sodium dodecylsulfonate) at 50° C., preferably at 55° C., more preferably at 62° C. and most preferably at 68° C., and more preferably for 1 hour with 0.2×SSC and 0.1% SDS at 50° C., preferably at 55° C., more preferably at 62° C. and most preferably at 68° C., a positive hybridization signal is still observed.

In another embodiment, the invention provides primers for producing the gene sequences according to the invention by amplification, for example, the polymerase chain reaction. The primers include the sense and antisense primers coding for the corresponding amino acid sequences. Suitable primers may in principle be obtained by methods known to the person skilled in the art. The discovery of primers according to the invention is carried out by comparison with known DNA sequences or by translation of the visually detected amino acid sequences into the codon of the organism under consideration (e.g. for Streptomyces: Wright et al., Gene 1992, 113, 55–65). Common features in the amino acid sequence of proteins of so-called superfamilies are also of use for this purpose (Firestine et al., Chemistry & Biology 1996, 3, 779–783). Further information relating to the above may be found in "Oligonucleotide synthesis: a practical approach", edited by M. J. Gait, IRL Press Ltd, Oxford Washington D.C., 1984; PCR Protocols: A guide to methods and applications, edited by M. A. Innis, D. H. Gelfound, J. J. Sninsky and T. J. White. Academic Press, Inc., San Diego, 1990. The following primers are most preferred:

DIFAAGDSA AS-Primer (SEQ ID NO:3)
MKVTVVGCT S-Primer (SEQ ID NO:4)

In another embodiment, the present invention relates to a process for the production of improved rec-NADH oxidases and rec-NADH oxidases obtained thereby or nucleic acids coding therefor, starting from the nucleic acids according to the invention coding for an NADH oxidase (NOX),
a) the nucleic acids are subjected to mutagenesis,
b) the nucleic acids obtained from a) are cloned in a suitable vector and this is transferred to a suitable expression system, and
c) the proteins formed having an improved activity and/or selectivity are detected and isolated. This process may be executed once or any desired number of times in succession.

The procedure for improving the enzymes according to the invention by mutagenesis methods has long been known to the person skilled in the art. As mutagenesis methods there may be used all methods for this purpose available to the person skilled in the art. In particular these include saturation mutagenesis, random mutagenesis, shuffling methods as well as site-directed mutagenesis (Eigen M. and Gardinger W. (1984) Evolutionary molecular engineering based on RNA replication. *Pure & Appl. Chem.* 56(8), 967–978; Chen & Arnold (1991) Enzyme engineering for nonaqueous solvents: random mutagenesis to enhance activity of subtilisin E in polar organic media. *Bio/Technology* 9, 1073–1077; Horwitz, M. and L. Loeb (1986) "Promoters Selected From Random DNA-Sequences" *Proceedings Of The National Academy Of Sciences Of The United States Of America* 83(19): 7405–7409; Dube, D. and L. Loeb (1989) "Mutants Generated By The Insertion Of Random Oligonucleotides Into The Active-Site Of The Beta-Lactamase Gene" *Biochemistry* 28(14): 5703–5707; Stemmer PC (1994). Rapid evolution of a protein in vitro by DNA shuffling. *Nature.* 370; 389–391 and Stemmer P C (1994) DNA shuffling by random fragmentation and reassembly: In vitro recombination for molecular evolution. *Proc Natl Acad Sci USA.* 91; 10747–10751).

The new nucleic acid sequences that are obtained are cloned according to the methods specified hereinafter in a host organism (literature, see below) and the expressed enzymes are detected and then isolated using suitable screening methods (Roberts J., Stella V. J. and Decedue C. J. (1985) A colorimetric assay of pancreatic lipase: rapid detection of lipase and colipase separated by gel filtration. *Lipids* 20(1): 42–45; Pratt R. F., Faraci W. S. and Govardhan C. P. (1985) A direct spectrophotometric assay for D-alanine carboxypeptidases and for the esterase activity of beta-lactamases. *Anal. Biochem.* 144(1): 204–206; Brückner, H., R. Wittner, and H. Godel (1991) Fully automated high-performance liquid chromatographic separation of DL-amino acids derivatized with o-Phthaldialdehyde together with N-isopropyl-cysteine. Application to food samples).

The present invention also provides using NADH oxidase (NOX) according to the invention, optionally improved by mutation, for the production of chiral enantiomer-enriched organic compounds such as, for example, alcohols or amino acids. Such compounds are used in a similar manner as described in DE 10037101, Enzyme Catalysis in Organic Synthesis, Ed.: K. Drauz, H. Waldmann, VCH, 1$^{st}$ Edition.

The nucleic acids according to the invention and improved still further that code for the NADH oxidase (NOX) as described herein, are preferably suitable for the production of whole-cell catalysts (DE10037115.9 as well as the literature cited therein). The invention provides a whole-cell catalyst containing a cloned gene for a dehydrogenase and a cloned gene for an NADH oxidase. Preferably the whole-cell catalyst according to the invention should contain an NADH oxidase (NOX) from Lactobacillus. More preferably, NADH oxidase is from *Lactobacillus brevis*, including *Lactobacillus brevis* DSM 20054 or *Lactobacillus kefir* DSM 20587. The production of such an organism is known to the person skilled in the art (PCT/EP00/08473; PCT/US00/08159; relevant literature, see below).

The advantage of such an organism is the simultaneous expression of both enzymes, whereby only a rec-organism still has to be used for the reaction. In order to match the expression of the enzymes with respect to their reaction rates, the coding nucleic acids may be carried on various plasmids having different copy numbers and/or promoters of different strengths may be used. In one embodiment, the enzymes are encoded on plasmids with similar copy numbers in a host cell; and/or under the control of promoters of similar strength. With enzyme systems matched in this way there is advantageously no accumulation of a possible inhibiting intermediate compound(s), and the reaction under consideration may proceed at an optimal overall rate. This is described in PCT/EP00/08473; and Gellissen et al., *Appl. Microbiol. Biotechnol.* 1996, 46, 46–54.

In a process for producing NADH oxidase from Lactobacillus advantageous expression of the NADH oxidase (NOX) the microorganism can be acheived by cultivating the microorganism under aerobic conditions.

It has been found that Lactobacillus grows significantly better in a standard medium under aerobic conditions than under the otherwise conventional anaerobic conditions. It is preferred to use a *Lactobacillus brevis*, preferably *Lactobacillus brevis* DSM 20054, or *Lactobacillus kefir* DSM 20587. According to the invention those conditions considered aerobic are those in which the microorganism, when cultivated in flasks as a shaken culture or when cultivated in a fermenter, is grown in the presence of measurable concentrations of oxygen. The expression "measurable oxygen concentration" is understood to mean that the dissolved oxygen is 1% of the saturation value for oxygen, the oxygen being measured under otherwise normal conditions with an oxygen electrode.

The nucleic acids according to the invention can be used for the production of rec-NADH oxidase (NOX). Recombinant techniques known in the art (see below) can be used to produce the enzymes described herein in an amount sufficient for an industrial process from host cells carrying the nucleic acids encoding the enzyme. The production of the rec-enzymes according to the invention is carried out by genetic engineering processes as described in, for example, Sambrook et al. 1989, Molecular cloning: A Laboratory Manual, 2nd Edition, Cold Spring Harbor Laboratory Press, Balbas P & Bolivar F. 1990; Design and construction of expression plasmid vectors in *E. coli, Methods Enzymology* 185, 14–37; Vectors: A Survey of Molecular Cloning Vectors and Their Uses. R. L. Rodriguez & D. T. Denhardt, Eds: 205–225). With regard to the general procedure (PCR and fusion PCR, inverse PCR, cloning, expression etc.), reference may be made to the following literature and the references cited therein: Riley J, Butler R, Finniear R, Jenner D, Powell S, Anand R, Smith J C, Markham A F (1990). A novel, rapid method for the isolation of terminal sequences from yeast artificial chromosome (YAC) clones. *Nucl Acids Res.* 18, 8186; Triglia T, Peterson M G, Kemp D J (1988). A procedure for in vitro amplification of DNA segments that lie outside the boundaries of known sequences. *Nucleic Acids Res.* 16, 8186; Sambrook J, Fritsch E F, Maniatis T (1989). Molecular Cloning. Cold Spring Harbour Laboratory Press; Vectors: A Survey of Molecular Cloning Vectors and Their Uses. R. L. Rodriguez & D. T. Denhardt, II.

The enzymes described herein may be used in the free form as homogeneously purified compounds, or as enzyme produced by recombinant technology. Furthermore the enzyme may also be employed as a constituent of an intact host organism or in conjunction with the macerated cell mass of the host organism purified to an arbitrarily high degree. It is also possible to use the enzymes in immobilised form (Bhavender P. Sharma, Lorraine F. Bailey and Ralph A. Messing, "Immobilisierte Biomaterialiern—Techniken and Anwendungen", Angew. Chem. 1982, 94, 836–852). The immobilisation is preferably carried out by lyophilisation (Dordick et al. J. Am. Chem. Soc. 194, 116, 5009–5010; Okahata et al. Tetrahedron Lett. 1997, 38, 1971–1974; Adlercreutz et al. Biocatalysis 1992, 6, 291–305). It is most particularly preferred to carry out the lyophilisation in the presence of surfactants such as aerosol OT, polyvinylpyrrolidone, polyethylene glycol (PEG) or Brij 52 (diethyleneglycolmonocetyl ether) (Goto et al. Biotechnol. Techniques 1997, 11, 375–378). The use as CLECs is also possible (St Clair et al. Angew Chem Int Ed Engl 2000 Jan, 39(2), 380–383).

The expression "optically enriched (enantiomer-enriched) compounds" within the scope of the invention is understood to mean the presence of an optical antipode in a mixture with the other antipode, in an amount greater than 50 mole %.

*Lactobacillus brevis* DSM 20054 and *Lactobacillus kefir* DSM 20587 have been filed at the German Collection for Microorganisms and Cell Cultures (DSMZ-Deutsche Sammlung von Mikroorganismen und Zelkulturen GmbH, Mascheroder Weg 1b, D-38124, Braunschweig, Germany) under the corresponding number and is accessible to the public.

The expression "nucleic acids" includes all types of single-strand or double-strand DNA, as well as, RNA or mixtures thereof.

The expression "improved rec-enzymes" as used herein means those that enzymes that have a modified substrate spectrum, are more active and/or more selective, or are more stable under the employed reaction conditions. For example, improved rec-enzymes may be those that are at least 1% (including at least 2, 3, 4, 5, 10, 15, 20% etc.) more active, more stable, and/or more selective than an enzyme which has not been modified, e.g., improved relative to the enzyme containing the amino acid sequence in SEQ ID NO:2.

Included within the present invention are protein sequences and nucleic acid sequences that exhibit an homology (exclusive of the natural degeneration) greater than 80%, preferably greater than 90%, 91%, 92%, 93% or 94%, more preferably greater than 95% or 96%, and particularly preferably greater than 97%, 98% or 99% with respect to one of these sequences, provided that the mode of action and/or purpose of such a sequence is retained, e.g., enzymatic activity. The expression "homology" (or identity) as used herein may be defined by the equation H (%)=[1−V/X]×100, where H denotes homology, X is the total number of nucleotide bases/amino acids of the comparison sequence, and V is the number of different nucleotide bases/amino acids of the sequence under consideration, referred to the comparison sequence. In any case the term "nucleic acids coding for amino acid sequences" covers all sequences that appear possible according to the degeneration of the genetic code.

Having generally described this invention, a further understanding can be obtained by reference to certain specific examples which are provided herein for purposes of illustration only, and are not intended to be limiting unless otherwise specified.

EXAMPLES

1) Cultivation of *Lactobacillus brevis* for Obtaining NADH Oxidase

*Lactobacillus brevis* DSM 20054 was cultivated in a standard medium for lactobacillae. In this connection it was found that the strain grew significantly better under the addition of oxygen than under the anaerobic conditions that are in fact normally used for lactobacillus strains. An enzyme test on the activity of an NADH oxidase showed that the strain particularly under these unusual cultivation conditions exhibits a high activity of an NADH oxidase (NOX).

For the enzyme purification and characterisation cells were therefore cultivated under the following conditions:

Medium: Pro 1 L: 10 g caseine peptone, tryptically digested; 10 g meat extract; 5 g yeast extract; 20 g glucose; 1 g Tween 80; 2 g $K_2HPO_4$; 5 g Na acetate; 2 g diammonium citrate; 0.2 g $MgSO_4 \times 7H_2O$; 0.05 g $MnSO_4 \times H_2O$; pH=6.2–6.5.

Cultivation is carried out in a shaken flask (equipped with 2 baffles) at 30° C. for 2 days while stirring. The cell mass is then obtained by centrifugation and may be stored at −20° C. for a relatively long time.

2) Enzyme Isolation a) Crude Extract Production

The cells were macerated by wet grinding with glass beads. For this, the moist bacterial mass (10 g) was suspended in 0.1 M sodium acetate buffer, pH 4.5 (30 ml) and macerated by grinding in a stirred cell glass bead mill (SCP disintegrator, Innomed-Konsult AB, Sweden) at 4000 rpm for 20 minutes. The macerated cells were centrifuged off and the supernatant was identified as crude extract.

The selected pH value of 4.5 has a decisive influence on the enzyme yield in the crude extract; under these conditions a crude extract preparation is obtained having a specific activity of 17.8 U/mg and a yield of 700 units, whereas when using a buffer with a pH of 7.4 the specific activity was only 2.6 U/mg and the yield was 580 units.

The enzyme activity was measured by means of the following photometric test (340 nm, 30° C. measurement temperature): 0.1 mM NADH; 100 mM potassium phosphate buffer pH 7.5; 1 mM DTT (=dithiothreitol); 10 μl enzyme solution per 1 ml (diluted if necessary). 1 unit NADH oxidase activity oxidises 1 μMole NADH/min.

b) Chromatographic Purification of the Enzyme

After the preparation of the crude extract in buffer with a pH of 4.5, the crude extract was immediately rebuffered and transferred to a Macro Q column (Biorad) equilibrated with 50 mM TEA pH 7.5+3 mM DTT+200 mM NaCl (=buffer A) (100 ml column volume, flow rate 4 ml/min, 10 ml fractions). The chromatography was carried out on an FPLC apparatus (Pharmacia) (pressure 0.1 MPa, room temperature). The proteins were eluted by means of an NaCl step gradient to 1 M NaCl (buffer B: buffer A+1 M NaCl), the following steps being used: 0–2 column volumes: 0% B (=200 mM NaCl), 2–5 column volumes: 40% B, 5–5.5 column volumes: 100% B. The enzyme activity and the protein content in the fractions were determined by means of the photometric test. The active fractions were combined and concentrated by evaporation in an Amicon stirred cell (YM10 membrane, 50 ml) while simultaneously rebuffering with hydroxylapatite equilibration buffer, see below.

This fraction pool was added to an hydroxylapatite ceramic type 20 μm column (Biorad) equilibrated with 10 mM Kpi buffer pH 6.7+3 mM DTT+200 mM NaCl (=buffer A) (15 ml column volume, flow rate 2 ml/min, 5 ml fractions; FPLC apparatus, pressure 0.1 MPa, room temperature). The proteins were eluted with a 3-step gradient to 500 mM KPi (buffer B: buffer A+500 mM Kpi) with the following stages: 0–3 column volumes 0% B, 3–7 column volumes 30% B, 7–9 column volumes 50% B, then rising to 100% B in 3 column volumes. The active fractions were combined and concentrated as described above, and rebuffered with the buffer required for the phenylsepharose.

This preparation was added, after the addition of ammonium sulfate (1.2 M final concencentration in the sample), to a phenylsepharose High Sub column (Pharmacia) equilibrated with 50 mN TEA pH 7.5 +3 mN DTT +1.2 M $(NH_4)_2SO_4$ (=buffer A) (25ml column volume, flow rate 1 ml/min, 3 ml fractions; FPLC apparatus, pressure 0.1 MPa, room temperature). The proteins were eluted using a 3-step gradient to 0 M ammonium sulfate (buffer B: buffer A without ammonium sulfate) with the following stages: 1 column volume 0% B, 1 column volume 20% B, 1 column volume 60% B, 2 column volumes 100% B). The active fractions were combined, concentrated by evaporation in an Amicon ultrafiltration cell, followed by the addition of further ammonium sulfate.

The last purification stage, which was carried out with the concentrated fraction from the phenylsepharose High Sub column, is a fine purification by chromatography on phenylsepharose 650C material (Tosohaas), equilibrated with 50 mM TEA pH 7.5+3 mM DTT+1.2 M $(NH_4)_2SO_4$ (=buffer A). Chromatography conditions: column volume 2 ml, flow rate 1 ml/min; FPLC apparatus, pressure 0.1 MPa, room temperature, 2 ml fractions). The proteins are eluted with a 4-stage gradient to 0 M ammonium sulfate (buffer B: buffer A without ammonium sulfate) using the following stages: 10 column volumes 0% B, 5 column volumes 20% B, 5 column volumes 50% B, 5 column volumes 70% B, 10 column volumes 100% B).

The enzyme activity and protein yields of the various chromatography steps are summarised in Table 1.

TABLE 1

Purification of the NADH oxidase from *Lactobacillus brevis* DSM 20054 (OH-apatite = hydroxyapatite; PS = phenylsepharose)

| Sample | Activity [U/ml] | Specific Activity [U/mg] | Total Activity [U] | Yield [%] | Enrich-ment Factor |
| --- | --- | --- | --- | --- | --- |
| Crude extract | 35.1 | 17.8 | 702 | 100 | 1 |
| Macro Q | 77.3 | 10.4 | 270 | 38 | 0.6 |
| OH-apatite | 32.2 | 12.2 | 103 | 15 | 0.7 |
| PS | 44 | 58.6 | 87 | 12 | 3.3 |
| PS 650C | 98 | 116 | 98 | 14 | 6.5 |

An SDS-PAGE of the purified fractions according to Table 1 shows that the enzyme fraction after the last step still contains only 2 proteins, whose subunits have molecular weights of 38 and 50 kDa. These two protein bands can be individually N-terminally sequenced after blotting, and a comparison with sequences accessible in databanks shows that the 38 kDa band has very high similarities with known lactate dehydrogenases, while the 50 kDa band has very high similarities with NADH oxidases.

3) Biochemical Characteristic Data of the NADH Oxidase from *L. brevis*

The biochemical data were determined with an enzyme preparation purified by 4 chromatographic steps.

a) pH Dependence of the Oxidation

The pH optimum was measured in the range pH 4.0 to 10.0. Different buffers were used depending on the pH value. As a check on the influence of the buffer, when changing the buffer this pH value was measured twice in the different buffers (pH 7.0 and pH 8.5). 0.1 M citric acid/$Na_2PO_4$ was used for the range pH 4.0–7.0, 0.1 M TEA was used for the range 7.0–8.5, and 0.1 M glycine/NaOH was used for the range pH 8.5–10.0. FIG. 1 shows that the optimum of the NADH oxidation is at pH 8.0 to 8.5.

b) pH Stability of the NADH Oxidase

Figure 2:
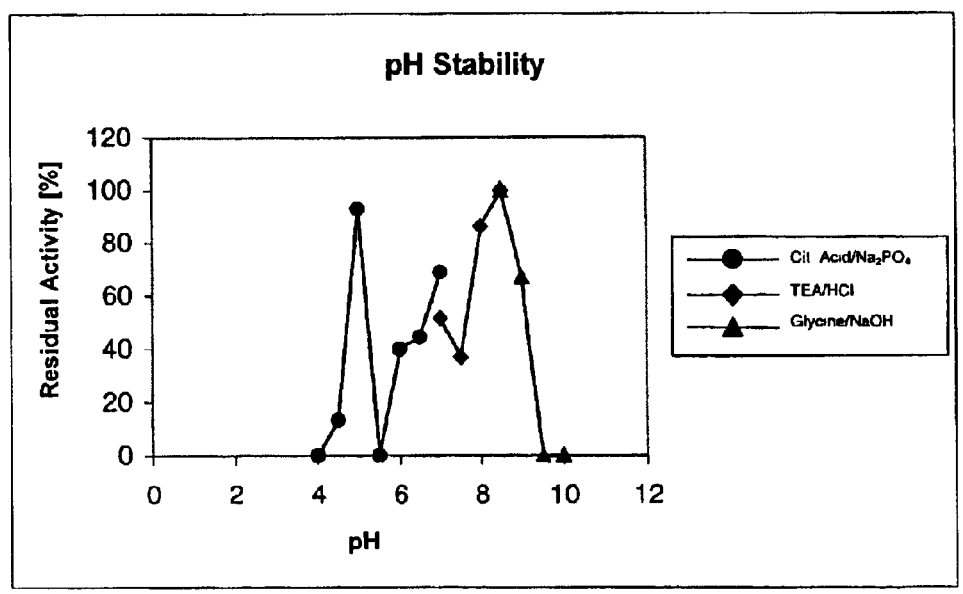
FIG. 2 shows NADH oxidation at varying conditions, pH, time, and buffer conditions.

In order to determine the pH stability the NADH oxidase was incubated for 8 hours in the buffers listed under 3a), then the residual activity was measured in the standard test. FIG. 2 shows that the enzyme has a first sharp stability optimum at pH 5.0, is moderately stable in the range 5.5–7.5, and exhibits a second optimum at pH 8.5. At pH 8.5 the enzyme is still up to 100% stable after 8 hours in TEA/NaOH buffer as well as in glycine/NaOH buffer. The figure illustrates that the enzyme stable in the slightly alkaline range (pH 8–9) is also stable in a wider range. This range is useful for application purposes if the NADH oxidase for the oxidation is to be coupled with an NAD-dependent dehydrogenase, since the pH optimum of many dehydrogenases for the oxidation lies in a slightly alkaline range.

c) Temperature Optimum of the NADH Oxidase

Figure 3:
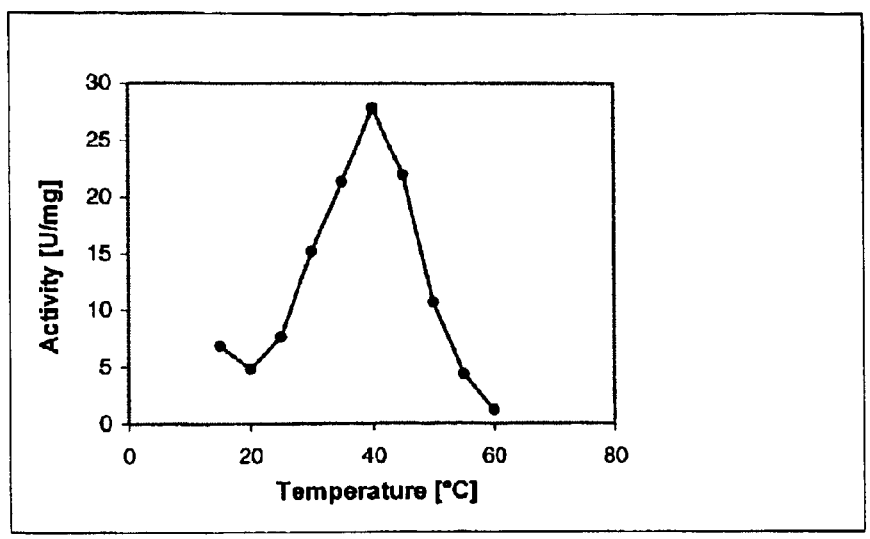
FIG. 3 shows the NADH oxidation at various temperature.

Activity tests at various temperatures show that the NADH oxidase exhibits maximum activity at 40° C. (FIG. 3).

d) Temperature Stability of the NADH Oxidase

In order to determine the temperature stability enzyme samples were stored at 30° C. and 42° C., samples were taken at various times, and the residual activity was measured. The evaluation shows that the enzyme at 30° C. is in practice stable for ca. 400 minutes, following which it appears to deactivate according to a slow reaction kinetics (half-value time ca. 18 hours). At 42° C. the enzyme deactivates initially (up to ca. 120 minutes) relatively quickly, following which it appears to be stable at ca. 50% residual activity over a relatively long time (at least 16 hours).

e) Determination of the KM Value for NADH for the NADH Oxidase

For the substrate NADH the concentration was varied in the range from 0.0013 to 0.52 mM and the activity was measured photometrically. The evaluation shows that maximum activity is reached at 0.1 mM. Higher NADH concentrations (up to 0.5 mM) exhibit only a weak excess inhibition. The Km value is calculated to be 24 µM. This high affinity of the enzyme for NADH is very advantageous for applications in which NAD+is to be regenerated by oxidation of NADH, since a prerequisite for this is as complete an oxidation of NADH as possible.

4) Protein Chemistry Characteristic Data of the NADH Oxidase from *Lactobacillus brevis* a) N-Terminal Amino Acid Sequence

The results of several enrichments always revealed a protein whose subunits have a molecular weight according to SDS-PAGE of 50 kDa. The first 27 amino acids of the N-terminus were determined for this protein (automated Edman decomposition with an automated sequencer 4774 (Applied Biosystems) with online HPLC 120 A); the sequence is as follows: MKVTVV GCTHAGTFAIKQILAEEPDADXXVY (SEQ ID NO:5). In the sequence a conserved motif is underlined that acts as FAD-binding motif in NADH oxidases, and is a slight modification of the known ADP-binding site GXGXXG (SEQ ID NO:6). Databank searches (BLAST) already show for this protein fragment agreement with known NADH oxidases.

a) Determination of the Protein and Gene Sequences

The results of the databank searches show in some partial regions sequences that are present in virtually all NADH oxidases or in related NADH peroxidases. The amino acid sequence DIFAAGDSA (SEQ ID NO:3) is regarded as such a conserved region. An antisense codon is used as "C-terminal" primer for this sequence, and together with a primer that codes for the N-terminus MKVTVVGCT (SEQ ID NO:4), is used in a PCR. The PCR yields a 777 bp long fragment that is 59% identical to the NADH oxidase (NOX) from Enterococcus. A gene library is established by digesting genome DNA with 4 different restriction endonucleases (EcoRV, Pvu II, Sca I and Stu I). Using specific primers derived from the cleavage sites of the restriction enzymes and sequences from the 777 bp fragment, further sequence fragments are then obtained by means of PCR, whereby the total sequence can be defined with the aid of overlapping DNA sequences and the stop codon.

The sequence for the NADH oxidase (NOX) from *L. brevis* is reproduced in the sequence protocol (Seq. 1) given above.

5) Use of the NADH Oxidase from *Lactobacillus brevis* for the Coenzyme Regeneration A typical use of the NADH oxidase is the regeneration of NAD+. This may be necessary for example if NAD-dependent dehydrogenases are used for the oxidation, as has been shown in a general way hereinbefore (reaction scheme 1). This is demonstrated in the following example for the production of an enantiomer-pure alcohol corresponding to the following equations:

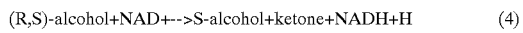
(R,S)-alcohol+NAD+-->S-alcohol+ketone+NADH+H    (4)

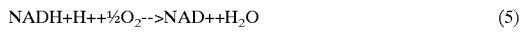
NADH+H++½O₂-->NAD++H₂O    (5)

with an R-specific alcohol dehydrogenase as catalyst for reaction (4), and the NADH oxidase for (5).

In this example an NAD mutant of the R alcohol dehydrogenase from *Lactobacillus brevis* (recADHG37D (NAD-mutant) DE10037101.9), coupled with the purified NADH oxidase from *Lactobacillus brevis*, was used as R-specific alcohol dehydrogenase. (R,S)-phenylethanol was used as alcohol, and the reaction was carried out as a batch reaction. The following reactants were used: 50 mM (R,S)-phenylethanol, 2 mM NADH, 50 mM TEA buffer pH 7.0 with 1 mM MgCl₂ and with 5 mM DTT, 1 U recADHG37D and 2 U NADH oxidase.

Figure 4:
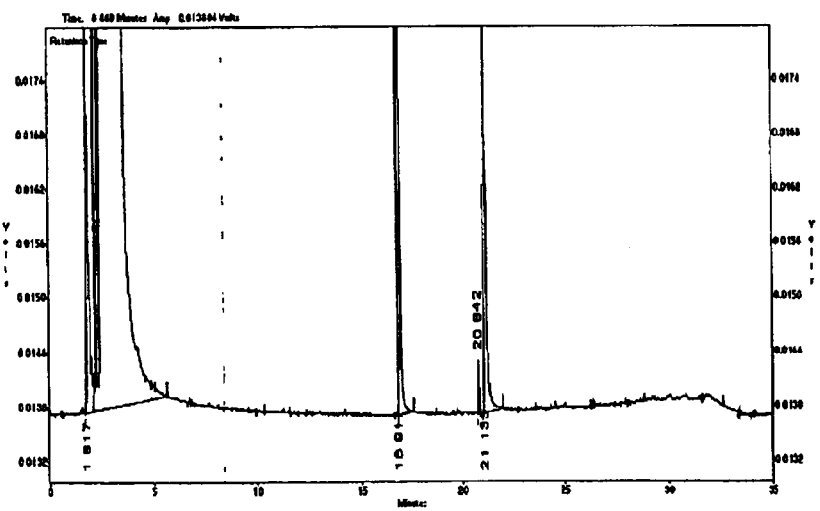
FIG. 4 shows the GC spectrum of a sample in which the R-alcohol had been almost completely oxidized.

Samples were taken after 0, 1, 2, 3, 4, 6, 9 and 24 hours and separated by gas chromatography (column: CP-Chirasil-DEX CB, length: 25 m, diameter: 25 μm (Chrompack). Temperature programme: 5 mins at 60° C., then 5° C./min up to 190° C.; column flow rate 1.3 ml/min; gas: helium. The acetophenone peak (product; retention time=16.9 min) as well as the enantiomers of phenylethanol (educts; retention times R-phenylethanol=20.8 min and S-phenylethanol=21.1 min) were detected. FIG. 4 shows the GC spectrum of a sample in which the R-alcohol had been almost completely oxidised, which is why a corresponding amount of the oxidation product acetophenone can be seen. As a control the same experiment was carried out, but without the addition of NADH oxidase. Gas chromatography analysis does not show any significant change in the two alcohols, and simply a small amount of acetophenone can be detected, which may possibly be attributed to a spontaneous oxidation of NADH by atmospheric oxygen.

The present application claims priority to German Application DE 101 40 088.8 filed on Aug. 16, 2002, the entire contents of which are incorporated herein by reference.

Obviously, numerous modifications and variations on the present invention are possible in light of the above teachings. It is therefore to be understood that within the scope of the appended claims, the invention may be practiced otherwise than as specifically described herein.

What is claimed is:

1. An isolated NADH oxidase obtained from *Lactobacillus*, which comprises SEQ ID NO: 2.

2. The isolated NADH oxidase according to claim 1, which is obtained from *Lactobacillus brevis*.

3. The isolated NADH oxidase according to claim 1, which is obtained from *Lactobacillus brevis* DSM 20054.

* * * * *

SEQUENCE LISTING

<160> NUMBER OF SEQ ID NOS: 6

<210> SEQ ID NO 1
<211> LENGTH: 1353
<212> TYPE: DNA
<213> ORGANISM: Lactobacillus brevis
<220> FEATURE:
<221> NAME/KEY: CDS
<222> LOCATION: (1)..(1353)
<223> OTHER INFORMATION:

<400> SEQUENCE: 1

```
atg aaa gtc aca gtt gtt ggt tgt aca cat gcc gga acc ttt gcg att        48
Met Lys Val Thr Val Val Gly Cys Thr His Ala Gly Thr Phe Ala Ile
1               5                   10                  15 aaa caa atc ttg gcc gaa cac cct gat gcc gaa gtg acc gtc tac gaa        96
Lys Gln Ile Leu Ala Glu His Pro Asp Ala Glu Val Thr Val Tyr Glu
            20                  25                  30 cgt aac gat gtc att tca ttt ctc tct tgt gga atc gcc ctt tac ctg       144
Arg Asn Asp Val Ile Ser Phe Leu Ser Cys Gly Ile Ala Leu Tyr Leu
        35                  40                  45 ggg gga aaa gtc gct gat ccg caa ggc ctc ttt tat tca agt cct gaa       192
Gly Gly Lys Val Ala Asp Pro Gln Gly Leu Phe Tyr Ser Ser Pro Glu
    50                  55                  60 gaa ctc caa aaa tta ggc gct aat gtc caa atg aat cac aat gtt tta       240
```

```
                                                     -continued

Glu Leu Gln Lys Leu Gly Ala Asn Val Gln Met Asn His Asn Val Leu
 65              70                  75                  80 gcg atc gat cct gat caa aag aca gtg acc gtt gag gac tta acc agt       288
Ala Ile Asp Pro Asp Gln Lys Thr Val Thr Val Glu Asp Leu Thr Ser
                 85                  90                  95 cat gca caa acg act gag tca tac gat aaa cta gtc atg acg tct ggt       336
His Ala Gln Thr Thr Glu Ser Tyr Asp Lys Leu Val Met Thr Ser Gly
                100                 105                 110 tct tgg cca att gtc ccc aag att ccg ggc atc gat agc gat cgc gtt       384
Ser Trp Pro Ile Val Pro Lys Ile Pro Gly Ile Asp Ser Asp Arg Val
            115                 120                 125 aag ctc tgc aaa aac tgg gca cat gcg caa gct cta atc gaa gat gct       432
Lys Leu Cys Lys Asn Trp Ala His Ala Gln Ala Leu Ile Glu Asp Ala
        130                 135                 140 aag gaa gcc aag cgg att acc gtt att ggt gcc ggc tat att ggt gct       480
Lys Glu Ala Lys Arg Ile Thr Val Ile Gly Ala Gly Tyr Ile Gly Ala
145                 150                 155                 160 gaa cta gca gaa gcc tac tcc act act ggt cat gac gta acc tta att       528
Glu Leu Ala Glu Ala Tyr Ser Thr Thr Gly His Asp Val Thr Leu Ile
                165                 170                 175 gat gcg atg gac cgg gtt atg ccc aag tac ttt gat gct gat ttt acg       576
Asp Ala Met Asp Arg Val Met Pro Lys Tyr Phe Asp Ala Asp Phe Thr
                180                 185                 190 gat gtc att gaa caa gat tat cgg gat cac ggt gtc caa ctt gcc tta       624
Asp Val Ile Glu Gln Asp Tyr Arg Asp His Gly Val Gln Leu Ala Leu
            195                 200                 205 agt gaa acg gtt gaa agc ttt act gat agt gca act ggg ttg acc att       672
Ser Glu Thr Val Glu Ser Phe Thr Asp Ser Ala Thr Gly Leu Thr Ile
210                 215                 220 aag act gat aag aac agc tat gaa acg gat ctc gct att tta tgc att       720
Lys Thr Asp Lys Asn Ser Tyr Glu Thr Asp Leu Ala Ile Leu Cys Ile
225                 230                 235                 240 ggc ttt aga cca aat acc gac ctg ctg aaa ggc aaa gtc gat atg gca       768
Gly Phe Arg Pro Asn Thr Asp Leu Leu Lys Gly Lys Val Asp Met Ala
                245                 250                 255 cca aac ggc gcg att att acg gat gac tac atg cgt tct tct aac cct       816
Pro Asn Gly Ala Ile Ile Thr Asp Asp Tyr Met Arg Ser Ser Asn Pro
                260                 265                 270 gat att ttc gcc gct ggt gac agt gct gct gtg cac tac aac cca acc       864
Asp Ile Phe Ala Ala Gly Asp Ser Ala Ala Val His Tyr Asn Pro Thr
            275                 280                 285 cat cag aat gct tac att ccc tta gca act aac gcg gtg cgt caa ggt       912
His Gln Asn Ala Tyr Ile Pro Leu Ala Thr Asn Ala Val Arg Gln Gly
        290                 295                 300 atc cta gtc ggt aaa aac cta gtt aag ccg acc gtc aag tat atg gga       960
Ile Leu Val Gly Lys Asn Leu Val Lys Pro Thr Val Lys Tyr Met Gly
305                 310                 315                 320 aca caa tca tct tct ggt ttg gca ctc tat gat cgg acg atc gtc tca      1008
Thr Gln Ser Ser Ser Gly Leu Ala Leu Tyr Asp Arg Thr Ile Val Ser
                325                 330                 335 act ggt tta acg cta gca gct gca aaa caa caa ggg gtg aac gct gaa      1056
Thr Gly Leu Thr Leu Ala Ala Ala Lys Gln Gln Gly Val Asn Ala Glu
                340                 345                 350 caa gtg att gtt gaa gat aat tat cgc cca gag ttt atg ccg tca act      1104
Gln Val Ile Val Glu Asp Asn Tyr Arg Pro Glu Phe Met Pro Ser Thr
            355                 360                 365 gaa ccc gtt ttg atg tca tta gtc ttt gac ccc gac aca cac cgg atc      1152
Glu Pro Val Leu Met Ser Leu Val Phe Asp Pro Asp Thr His Arg Ile
        370                 375                 380
```

-continued

```
tta ggt ggt gcg tta atg agt aaa tac gat gtt tca caa tcg gcc aac     1200
Leu Gly Gly Ala Leu Met Ser Lys Tyr Asp Val Ser Gln Ser Ala Asn
385                 390                 395                 400 acc ctt tct gtt tgc atc caa aac gaa aat aca att gat gac tta gcg     1248
Thr Leu Ser Val Cys Ile Gln Asn Glu Asn Thr Ile Asp Asp Leu Ala
            405                 410                 415 atg gtt gat atg ctc ttc cag cct aac ttt gat cga cca ttc aac tac     1296
Met Val Asp Met Leu Phe Gln Pro Asn Phe Asp Arg Pro Phe Asn Tyr
        420                 425                 430 cta aac atc tta gcg caa gct gct cag gca aag gtt gcc caa tca gtt     1344
Leu Asn Ile Leu Ala Gln Ala Ala Gln Ala Lys Val Ala Gln Ser Val
            435                 440                 445 aac gct taa                                                          1353
Asn Ala
    450
```

<210> SEQ ID NO 2
<211> LENGTH: 450
<212> TYPE: PRT
<213> ORGANISM: Lactobacillus brevis

<400> SEQUENCE: 2

```
Met Lys Val Thr Val Gly Cys Thr His Ala Gly Thr Phe Ala Ile
1               5                   10                  15

Lys Gln Ile Leu Ala Glu His Pro Asp Ala Glu Val Thr Val Tyr Glu
            20                  25                  30

Arg Asn Asp Val Ile Ser Phe Leu Ser Cys Gly Ile Ala Leu Tyr Leu
        35                  40                  45

Gly Gly Lys Val Ala Asp Pro Gln Gly Leu Phe Tyr Ser Ser Pro Glu
    50                  55                  60

Glu Leu Gln Lys Leu Gly Ala Asn Val Gln Met Asn His Asn Val Leu
65                  70                  75                  80

Ala Ile Asp Pro Asp Gln Lys Thr Val Thr Val Glu Asp Leu Thr Ser
                85                  90                  95

His Ala Gln Thr Thr Glu Ser Tyr Asp Lys Leu Val Met Thr Ser Gly
            100                 105                 110

Ser Trp Pro Ile Val Pro Lys Ile Pro Gly Ile Asp Ser Asp Arg Val
        115                 120                 125

Lys Leu Cys Lys Asn Trp Ala His Ala Gln Ala Leu Ile Glu Asp Ala
    130                 135                 140

Lys Glu Ala Lys Arg Ile Thr Val Ile Gly Ala Gly Tyr Ile Gly Ala
145                 150                 155                 160

Glu Leu Ala Glu Ala Tyr Ser Thr Thr Gly His Asp Val Thr Leu Ile
                165                 170                 175

Asp Ala Met Asp Arg Val Met Pro Lys Tyr Phe Asp Ala Asp Phe Thr
            180                 185                 190

Asp Val Ile Glu Gln Asp Tyr Arg Asp His Gly Val Gln Leu Ala Leu
        195                 200                 205

Ser Glu Thr Val Glu Ser Phe Thr Asp Ser Ala Thr Gly Leu Thr Ile
    210                 215                 220

Lys Thr Asp Lys Asn Ser Tyr Glu Thr Asp Leu Ala Ile Leu Cys Ile
225                 230                 235                 240

Gly Phe Arg Pro Asn Thr Asp Leu Leu Lys Gly Lys Val Asp Met Ala
                245                 250                 255

Pro Asn Gly Ala Ile Ile Thr Asp Asp Tyr Met Arg Ser Ser Asn Pro
            260                 265                 270
```

```
                    -continued

Asp Ile Phe Ala Ala Gly Asp Ser Ala Ala Val His Tyr Asn Pro Thr
        275                 280                 285

His Gln Asn Ala Tyr Ile Pro Leu Ala Thr Asn Ala Val Arg Gln Gly
    290                 295                 300

Ile Leu Val Gly Lys Asn Leu Val Lys Pro Thr Val Lys Tyr Met Gly
305                 310                 315                 320

Thr Gln Ser Ser Ser Gly Leu Ala Leu Tyr Asp Arg Thr Ile Val Ser
                325                 330                 335

Thr Gly Leu Thr Leu Ala Ala Lys Gln Gln Gly Val Asn Ala Glu
            340                 345                 350

Gln Val Ile Val Glu Asp Asn Tyr Arg Pro Glu Phe Met Pro Ser Thr
        355                 360                 365

Glu Pro Val Leu Met Ser Leu Val Phe Asp Pro Asp Thr His Arg Ile
    370                 375                 380

Leu Gly Gly Ala Leu Met Ser Lys Tyr Asp Val Ser Gln Ser Ala Asn
385                 390                 395                 400

Thr Leu Ser Val Cys Ile Gln Asn Glu Asn Thr Ile Asp Asp Leu Ala
                405                 410                 415

Met Val Asp Met Leu Phe Gln Pro Asn Phe Asp Arg Pro Phe Asn Tyr
            420                 425                 430

Leu Asn Ile Leu Ala Gln Ala Ala Gln Ala Lys Val Ala Gln Ser Val
        435                 440                 445

Asn Ala
    450

<210> SEQ ID NO 3
<211> LENGTH: 9
<212> TYPE: PRT
<213> ORGANISM: Artificial Sequence
<220> FEATURE:
<223> OTHER INFORMATION: synthetic peptide

<400> SEQUENCE: 3

Asp Ile Phe Ala Ala Gly Asp Ser Ala
1               5

<210> SEQ ID NO 4
<211> LENGTH: 9
<212> TYPE: PRT
<213> ORGANISM: Artificial Sequence
<220> FEATURE:
<223> OTHER INFORMATION: synthetic peptide

<400> SEQUENCE: 4

Met Lys Val Thr Val Val Gly Cys Thr
1               5

<210> SEQ ID NO 5
<211> LENGTH: 31
<212> TYPE: PRT
<213> ORGANISM: Lactobacillus brevis
<220> FEATURE:
<221> NAME/KEY: misc_feature
<222> LOCATION: (28)..(28)
<223> OTHER INFORMATION: Xaa is any amino acid
<220> FEATURE:
<221> NAME/KEY: misc_feature
<222> LOCATION: (29)..(29)
<223> OTHER INFORMATION: Xaa is any amino acid

<400> SEQUENCE: 5

Met Lys Val Thr Val Val Gly Cys Thr His Ala Gly Thr Phe Ala Ile
```

-continued

```
              1               5              10              15

Lys Gln Ile Leu Ala Glu Glu Pro Asp Ala Asp Xaa Xaa Val Tyr
                             20              25              30

<210> SEQ ID NO 6
<211> LENGTH: 6
<212> TYPE: PRT
<213> ORGANISM: Artificial Sequence
<220> FEATURE:
<223> OTHER INFORMATION: synthetic peptide
<220> FEATURE:
<221> NAME/KEY: misc_feature
<222> LOCATION: (2)..(2)
<223> OTHER INFORMATION: Xaa is any amino acid
<220> FEATURE:
<221> NAME/KEY: misc_feature
<222> LOCATION: (4)..(4)
<223> OTHER INFORMATION: Xaa is any amino acid
<220> FEATURE:
<221> NAME/KEY: misc_feature
<222> LOCATION: (5)..(5)
<223> OTHER INFORMATION: Xaa is any amino acid

<400> SEQUENCE: 6

Gly Xaa Gly Xaa Xaa Gly
1               5
```